United States Patent
Esteve-Soler

(10) Patent No.: US 6,403,643 B1
(45) Date of Patent: *Jun. 11, 2002

(54) USE OF 2,5-DIHYDROXYBENZENESULFONIC DERIVATIVES FOR THE NORMALIZATION OF ENDOTHELIAL FUNCTION

(75) Inventor: Jose Esteve-Soler, Alta de Gironella, 58-62 08011 Barcelona (ES)

(73) Assignee: Laboratories del Dr. Esteve, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 09/625,879

(22) Filed: Jul. 26, 2000

Related U.S. Application Data

(63) Continuation of application No. 09/155,751, filed as application No. PCT/EP97/01709 on Apr. 3, 1997, now Pat. No. 6,147,112.

(51) Int. Cl.⁷ ............................................. A61K 31/255
(52) U.S. Cl. ........................................ 514/518; 514/517
(58) Field of Search .................................. 514/518, 517

(56) References Cited

U.S. PATENT DOCUMENTS

| | | |
|---|---|---|
| 3,947,448 A | 3/1976 | Esteve-Subirana |
| 4,038,390 A | 7/1977 | Esteve-Subirana |
| 4,513,007 A | 4/1985 | Courten et al. |
| 6,147,112 A * | 11/2000 | Esteve-Soler ............... 514/518 |

OTHER PUBLICATIONS

Burnett, Arthur, L., et al., Nitric Oxide: A Physiologic Mediator Of Penile Erection, *Science*, 257:401–403, (1992).
Durante, William, et al., Impairment of endothelium–dependent relaxation in aortae from spontaneously diabetic rats, *Br. J. Pharmacol.* 94:463–468, (1988).
J. Hladovec, Vasotropic Drugs, A Survey Based on Unifying Concept of their Mechanism of Action, *Arzneim Forsch/Drug Res.*, 25:(5):1073–1076, XP 00615253 1988.
Hull, E.M., et al., The Roles of Nitric Oxide in Sexual Function of Male Rats, *Neuropharmacology*, 33(11):1499–1504, (1994).
Huguet, Par, G., et al., Action d'un hémostatique, la cyclonamine, sur la perméabilité et la résistance capillaires. Etude complémentaire, *Thérapie*, 24:429–450, (1969).
Kostis, John B., M.D., et al., Central Nervous System Effects of HMG CoA Reductase Inhibitors: Lovastatin and Pravastatin on Sleep and Cognitive Performance in Patients with Hypercholesterolemia, *J. Clin. Pharmacol.*, 34:989–996, (1994).
Kugiyama, K., et al., Impairment of endothelium–dependent arterial relaxation by lysolecithin in modified low–density lipoproteins, *Nature*, 344:160–162 (1990).
Rajfer, J. et al., *Lancet* editorial, 1992, 340, 882–883.
Rajferm J., et al., Nitric Oxide as a Mediator of Relaxation of the Corpus Cavernosum in Response to Nonadrenergic, Noncholinergic Neurotransmission, *The New England Journal of Medicine*, 326:90–94, (1992).
Rosen, Raymond, M.D., Pharmacological Effects on Nocturnal Penile Tumescence (NPT), *The Pharmacology of Sexual Function and Dysfunction*, edited by J. Bancroft, Elsevier, *Science*, 277–287, (1995).
Saenz de Tejada, I. et al., Impaired Neurogenic and Endothelium–Mediated Relaxation of Penile Smooth Muscle from Diabetic Men with Impotence, *The New England Journal of Medicine*, 320:1025–1030, (1989).
Sim, A.K., et al., The Evaluation of the Effect of the Venous Tonic 263–E on Capillary Permeability in the Rabbit after Administration by Intradermal and Intravenous Routes, *Arzneim–Forsch./Drug Res.*, 31(I):962–965 1990.
Standl, Rudolf, Diabetische Mikroangiopathie XP 000615251, *Innere Medisin*, 48:140–149, (1993).
Thomas, J. et al., Action du dobésilate de calcuim sur la résistance et la perméabilité capillaires et sur le temps de saignement et l'adhésivité plaquettaire modifiés par le dextran, *Annales pharmaceutiques francaises*, 30(6):415–427, (1972).
Mathieu, et al., Effect of Quinones and phenols on noradrenalinic hypertension in the rat *Chemical Abstracts*, 84(1), p. 34, 310K *Janvier* (1976).

* cited by examiner

*Primary Examiner*—Theodore J. Criares
(74) *Attorney, Agent, or Firm*—Wood, Phillips, Katz, Clark & Mortimer

(57) ABSTRACT

A method for the use of 2,5-dihydroxybenzenesulfonic derivatives for normalizing endothelial function is disclosed. Preferred 2,5-dihydroxybenzenesulfonic derivatives are calcium dobesilate, ethamsylate and persilate.

5 Claims, No Drawings

USE OF 2,5-DIHYDROXYBENZENESULFONIC DERIVATIVES FOR THE NORMALIZATION OF ENDOTHELIAL FUNCTION

This application is a continuation application of U.S. patent application Ser. No. 09/155,751 filed Oct. 1, 1998, now U.S. Pat. No. 6,147,112, which is an application filed under 35 U.S.C. Sec. 371 as a national stage of international application PCT/EP97/01709, which was filed Apr. 3, 1997.

FIELD OF THE INVENTION

The present invention relates to the use of derivatives of dihydroxybenzenesulfonic acids and their physiologically acceptable salts for the manufacture of medicaments intended for the normalization of the endothelial function, for the treatment of sexual dysfunction, of vascular complications of diabetes and of vascular disorders of endothelial origin.

BACKGROUND OF THE INVENTION

Recent studies have demonstrated that calcium dobesilate, ethamsylate and persilate exert effects on the endothelium in the sense of facilitating endothelium-dependent vascular relaxation. This effect is observed both in normal animals and in those in which vascular aging has been produced experimentally by means of the administration of high doses of vitamin $D_2$. This activity of calcium dobesilate, of ethamsylate and of persilate may be reflected in man by effects which are therapeutically useful. In particular, it has been demonstrated that the erection of the penis is modulated by nitric oxide produced in the endothelium (A. L. Burnett et al., Science, 1992, 257, 401–403; J. Kajfer et al., N. Engl. J. Med., 1992, 326, 90–94; Editorial, Lancet, 1992, 340, 882–883) and that, under circumstances where the endothelial function is detrimentally affected, as in hyperlipidemias (K. Kugiyama et al., Nature, 1990, 344, 160–162), correction of the detrimental change normalizes the erectile function, measured with accuracy during nocturnal sleep (J.-B. Kostis et al., J. Clin. Pharmacol., 1994, 34, 989–996; R. C. Rosen, "The Pharmacology of Sexual Function and Dysfunction", edited by J. Bancroft, Elsevier Sc., 1995, cages 277–287). The normalization of the endothelial function obtained with calcium dobesilate, ethamsylate and persilate can represent an entirely novel therapeutic approach to the problem of impotence (I. Saenz de Tejada et al., N. Engl. J. Med., 1989, 320, 1025–1030), both in patients with vascular disorders with various causes (diabetes, arteriosclerosis, and the like) and in patients where only a functional disorder can be detected.

Furthermore, the normalizing effect on the endothelial function can also offer therapeutic opportunities in vascular spasm processes, in complications of diabetes (W. Durante et al., Br. J. Pharmacol., 1988, 94, 463–468) and in all disorders, including premature ejaculation (E. M. Hull et al., Neuropharmacology, 1994, 33, 1499–1504), where a deficit in the formation of nitric oxide for the vascular endothelium appears evident.

BRIEF SUMMARY OF THE INVENTION

The compounds recommended in the context of the present invention correspond to the general formula I:

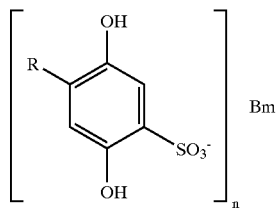

in which:
R represents a hydrogen atom (H) or a sulfonic group $(SO_3—)$
B represents a calcium atom (Ca++) or a diethylamine group $[H_2N+(C_2H_5)_2]$
n represents 1 or 2
m represents 1 or 2.

DETAILED DESCRIPTION OF THE INVENTION

The compounds of the examples which are shown below are prepared according to the processes described subsequently:

EXAMPLE 1

Calcium 2,5-dihydroxybenzenesulfonate (calcium dobesilate). "The Merck Index", 11th edition, Merck & Co., Rahway, N.J., USA, 1989.

EXAMPLE 2

Diethylamine 2,5-dihydroxybenzenesulfonate (ethamsilate). "The Merck Index", 11th edition, Merck & Co., R. Rahway, N.J., USA, 1989.

EXAMPLE 3

Bis(diethylamine) 2,5-dihydroxybenzene-1,4-disulfonate (bis(diethylamine) persilate). French Patent FR 73/17709 (Publication No. 2,201,888).

In order to study the normalizing effect on the endothelial function of the products which are the subject-matter of the present invention, various "in vitro" and "in vivo" studies have been carried out. A description is given below of the results obtained, as non-limiting example, with one of the products which are the subject-matter of the present invention, calcium dobesilate, it being demonstrated that it has an endothelium-dependent relaxing activity.

The studies were carried out by using the aortas isolated from male rabbits according to the techniques described by A. Quintana et al. (Europ. J. Pharmacol., 1978, 53, 113–116) and by the group from the University of Edinburgh (Pharmacological Experiments on Isolated Preparations, Edinburgh, Livingstone, 1970). The aortas isolated without the endothelium are prepared according to the technique described by R. Furchgott et al. (J. Cardiol. Pharmacol., 1984, 6, p. 336-p. 343).

A. "In vitro" Studies
1) Effect on the contraction of the aorta maintained with $10^{-6}$ M noradrenalin.
   Calcium dobesilate relaxes the contraction of noradrenalin in a way dependent on the concentration (between $10^{-4}$M and $10^{-11}$M). The maximum relaxation was 70%.
2) Effect on the basal tension in the aorta arteries with and without endothelium (basal tension=2 grams).

Calcium dobesilate at concentrations between $10^{-8}$M and $10^{-4}$ relaxes, in a dose-dependent way, the aortas subjected to a basal tension of 2 grams. The maximum relaxation was 44% for the arteries with endothelium and 48% for the arteries without endothelium.

3) Effect on the noradrenalin concentration/effect curve.

In arteries with the intact endothelium, calcium dobesilate at a concentration of $10^{-6}$M inhibits a 44% the contraction obtained with $10^{-4}$M noradrenalin. In contrast, with arteries without endothelium, there is no modification of the curve.

"In Vivo Studies"

The protective effect on the endothelium with calcium dobesilate was studied in the rabbit.

To do this, the arterial endothelium in rabbits is damaged by a daily treatment with an overdose of vitamin $D_2$ and three groups of animals are used in the study:

O—Control

I—Hypervitaminosis $D_2$

II—Hypervitaminosis $D_2$+50 mg/kg/day calcium dobesilate.

The studies are carried out with arteries originating from the treated rabbits by measuring the effect on the contraction of the aorta maintained with $10^{-6}$M noradrenalin.

Calcium dobesilate (between $10^{-11}$M and $10^{-5}$M) relaxes in a dose-dependent way the contraction due to noradrenalin. The least relaxation corresponds to the hypervitaminosis $D_2$ group (group I), whereas the maximum relaxation is obtained with the aortas of the group treated with calcium dobesilate (group II).

The maximum relaxation obtained for each group was as follows:

Group O (control): 69%

Group I (hypervitaminosis $D_2$: 52% M

Group II (hypervitaminosis $D_2$+calcium dobesilate): 100%

The results obtained show that calcium dobesilate acts by potentiating the synthesis and/or the release or else by decreasing the destruction of a releasing factor which depends on the vascular endothelium and which is probably released by noradrenalin through its action on the $\alpha_2$-adrenergic receptions.

In human therapeutics, the administration dose is, of course, a function of the seriousness of condition to be treated. It will generally be between approximately 0.5 and approximately 2 g/day. The derivatives of the invention will, for example, be administered in the form of hard gelatin capsules or tablets. Two specific pharmaceutical dosage forms will be shown below, by way of examples.

Example of Hard Gelatin Capsule Formula

| Calcium dobesilate | 0.500 g |
|---|---|
| Cellulose | 0.023 g |
| Magnesium estearate | 0.007 g |
| Colloidal silicon dioxide | 0.005 g |
| | 0.535 g |

Example of Tablet Formula

| Calcium dobesilate | 0.2500 g |
|---|---|
| Maize starch | 0.0650 g |
| Lactose | 0.0520 g |
| Povidone K-30 | 0.0175 g |
| Citric acid monohydrate | 0.0125 g |
| Magnesium estearate | 0.0020 g |
| Sodium bisulfite | 0.0010 g |
| | 0.4000 g |

On account of the advantageous pharmacological properties attached to the compounds of general formula I, the present invention applies to the application of these compounds as medicaments, to the pharmaceutical compositions comprising them and to their use for the manufacture of medicaments intended for the normalization of the endothelial function, for the treatment of sexual dysfunction, of vascular complications of diabetes and of vascular disorders of endothelial origin.

What is claimed is:

1. A method for normalizing endothelial function comprising administering to a patient in need of such normalizing an effective amount of a 2,5-dihydroxybenzene sulfonic compound of general formula I:

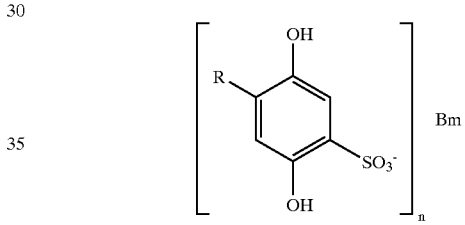

in which

R represents H or $SO_3^-$;

B represents $Ca^{++}$ or $H_2N©_2H_5)_2$;

n represents 1 or 2; and m represents 1 or 2.

2. The method of claim 1 wherein the effective amount is between 0.5 and 2.0 g/day.

3. The method of claim 1 wherein said compound of general formula I is calcium 2,5-dihydroxybenzenesulfonate.

4. The method of claim 1 wherein said compound of general formula I is diethylamide 2,5-dihydroxybenzenesulfonate.

5. The method of claim 1 wherein said compound of general formula I is bis(diethylamide) 2,5-dihydroxybenzene-1,4-disulfonate.

* * * * *

UNITED STATES PATENT AND TRADEMARK OFFICE
CERTIFICATE OF CORRECTION

PATENT NO.    : 6,403,643 B1                                      Page 1 of 1
DATED         : June 11, 2002
INVENTOR(S)   : Jose Esteve Soler It is certified that error appears in the above-identified patent and that said Letters Patent is hereby corrected as shown below:

Column 1,
Line 10, insert:
-- and which claims the priority of French patent application No. 9604182 with an application date of 03 April 1996 -- before ".".

Signed and Sealed this

Nineteenth Day of August, 2003

JAMES E. ROGAN
*Director of the United States Patent and Trademark Office*